United States Patent [19]

Hunziker

[11] 3,979,262

[45] Sept. 7, 1976

[54] COMPOSITIONS AND METHODS FOR THE DETERMINATION OF OXIDIZING AGENTS

[75] Inventor: Paul Hunziker, Basel, Switzerland

[73] Assignee: Hoffmann-La Roche Inc., Nutley, N.J.

[22] Filed: Feb. 11, 1975

[21] Appl. No.: 548,939

[30] Foreign Application Priority Data

Feb. 12, 1974 Switzerland.......................... 2150/74

[52] U.S. Cl.................. 195/103.5 R; 195/103.5 C; 195/99
[51] Int. Cl.$^2$........................ C12K 1/04; C12K 1/10
[58] Field of Search............... 195/103.5 C, 103.5 R, 195/99

[56] References Cited
UNITED STATES PATENTS 2,970,945 2/1961 Free et al...................... 195/103.5 R
3,862,885 1/1975 Kano et al..................... 195/103.5 R

OTHER PUBLICATIONS

N. Gochman et al., "Automated Determination of Uric Acid, With Use of a Uricase-Peroxidase System," Clin. Chem., vol. 17, No. 12, pp. 1154-1159, (1971).

Primary Examiner—A. Louis Monacell
Assistant Examiner—C. A. Fan
Attorney, Agent, or Firm—Samuel L. Welt; Bernard S. Leon; William M. Farley

[57] ABSTRACT

Compositions and methods are described for the determination of specific components in a biological fluid by a quantitative colorimetric determination of an oxidizing agent, e.g., hydrogen peroxide, produced in the biological fluid by an appropriate enzyme, said compositions comprising an aromatic amine component, a hydrazone component and a citric and/or maleic acid component.

22 Claims, No Drawings

COMPOSITIONS AND METHODS FOR THE DETERMINATION OF OXIDIZING AGENTS

BACKGROUND OF THE INVENTION

Many diagnostic tests for a component of a biological fluid result in the formation of an oxidizing agent such as hydrogen peroxide as a product. There is need, therefore, for a quantitatively accurate method for the determination of such oxidizing agents. For example, a successful method for the determination of glucose involves the treatment of the biological fluid containing glucose with glucoseoxidase to yield, inter alia, hydrogen peroxide as a product. The amount of hydrogen peroxide formed is then determined to measure the glucose content. Further, in the determination of uric acid in a biological fluid by the enzymatic method, any uric acid present is converted by uricase into allantoin and hydrogen peroxide. Subsequent determination of the peroxide formed provides the uric acid content. Also, cholesterol content is determined, after prior cleavage of cholesterol esters, using cholesteroloxidase, from the hydrogen peroxide formed.

However, such compositions and methods to be useful for the determination of the oxidizing agent formed must meet certain criteria, i.e., they must be adaptable to use with small amounts of specimen, must be simple enough to be used effectively in a clinical situation and must be sufficiently economical for mass screening. In addition, the method must be readily adaptable to an automated sequential or continuous flow system in order that a great many samples may be processed rapidly and with the highest possible accuracy. Further the composition used must have sufficient stability on storage to be readily available in clinical laboratories. Finally, the color developed must have sufficient sensitivity, i.e., be of a high intensity and have a favorable absorption region, i.e., such as not to be interfered with by the absorption regions of the other materials present.

In the glucose, uric acid and cholesterol tests mentioned above, hydrogen peroxide which results from the enzymatic conversion is colorimetrically determined by an additional step utilizing peroxidase and a color-forming composition, i.e. a chromogen. The following illustrates the reaction

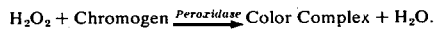

$H_2O_2$ + Chromogen $\xrightarrow{Peroxidase}$ Color Complex + $H_2O$.

One chromogen which has been so used is o-dianisidine, $[C_6H_3(OCH_3)NH_2]_2$. However, the color complex formed using this compound not only has a slight sensitivity (low color intensity) but also has absorption peaks in an unfavorable region (420–460 nm).

Another chromogen, proposed by W. Gochman and J. M. Schmitz [in Clinical Chemistry, vol. 17, No. 12, pp. 1154–1159 (1971)] is a mixture of 3-methyl-2-benzothiazole-hydrazone hydrochloride and N,N-dimethylaniline. This chromogen produces a color of high intensity which has absorption peaks in a favorable region (590–600 nm). However, this mixture has very poor shelf stability—i.e., less than a day—and thus is not amenable to routine use in a clinical laboratory.

Use of the compositions of this invention provides a reliable, convenient method for determining the quantity of oxidizing agent which results from enzymatic treatment of biological fluids. The method, using the compositions of this invention, is adapable for use in an automated sequential or continuous flow system as well as manual systems. Further, the compositions and methods of this invention overcome many of the disadvantages of the prior art compositions and methods. The compositions of this invention have greater shelf and storage stability than the prior art compositions and when used according to the method of this invention result in a developed color which has desirable intensity and absorption characteristics.

BRIEF SUMMARY OF THE INVENTION

The compositions of this invention comprise
a. as a first component, an amine
b. as a second component, a hydrazone and
c. as a third component, a buffer These compositions function as chromogens when they are added to a biological fluid previously treated to produce an oxidizing agent. The chromogen function is produced when an enzyme which causes the oxidative coupling of the amine and hydrazone components in the presence of the oxidizing agent is added to the treated biological fluid. Typical of such enzymes is peroxidase which is used when hydrogen peroxide is the oxidizing agent. The resulting colored solution can be evaluated by standard colorimetric procedures to provide a quantitative measure of the oxidizing agent content. The method can, of course, also be used to qualitatively detect the presence of a particular constituent in the biological fluid.

DETAILED DESCRIPTION OF THE INVENTION

Compositions for the colorimetric determination of oxidizing agents, as encompassed by this invention, comprise:
a. as the first component, an amine selected from the group consisting of an aromatic amine and an acid addition salt thereof with the proviso that substituents on the aromatic amine are not simultaneously in the ortho and para positions;
b. as the second component, a compound which is capable of oxidatively coupling with the aromatic amine of the first component to form a colored entity selected from the group of a hydrazone and an acid addition salt thereof and
c. as the third component, a buffer selected from the group consisting of citric acid, maleic acid and mixtures of citric acid and maleic acid.

The term "aromatic amine" as used throughout this specification includes aromatic amines which are either substituted or unsubstituted on the aromatic nucleus. The amines can be either primary, secondary or tertiary with aniline derivatives, naphthylamines or naphthylamine derivatives the preferred aromatic amines. An especially preferred aromatic amine unsubstituted on the aromatic nucleus is N,N-dimethylaniline. Where the aromatic amine has substitutes on the aromatic nucleus, the preferred substituents are lower alkyl, lower alkoxy, hydroxy, halogen, alkylthio, mercapto, amino, mono(lower alkyl)amino and di(lower alkyl)amino. The amino substituent is especially preferred. In no case is the aromatic amine substituted in both the ortho and para positions.

As used throughout this specification, the term "lower alkyl" either alone or in combination includes both straight or branched chain alkyl groups having from 1 to 7 carbon atoms such as methyl, ethyl, isopropyl and the like. The term "lower alkoxy" includes straight or branched chain alkoxy groups containing from 1 to 7 carbon atoms such as methoxy, ethoxy, propoxy and the like. The term "halogen" includes fluorine, chlorine, bromine and iodine.

Suitable aromatic amines substituted on the aromatic nucleus include m-phenylenediamine, o-chloroaniline, 1-naphthyl amine, o-toluidine, p-aminophenol and 2-naphthylamine.

The hydrazones of the second component are condensation products of a hydrazone with an aldehyde or ketone and contain the grouping >C=N H—.

Hydrazones which are capable of oxidatively coupling with the aromatic amines used in this invention to form a colored entity include but are not limited to: N-methyl-2-benzothiazolinone-hydrazone, N-methyl-pyridone-4-hydrazone, N-methyl-pyridone-2-hydrazone, N-methyl-quinolinone-2-hydrazone, N-methyl-quinolinone-4-hydrazone, N-methyl-2-benzothiazolinonehydrazone, N-methyl-thiazolinone-2-hydrazone, N-methyl-4-phenylthiazolinone-2-hydrazone, N-methyl-oxazolinone-2-hydrazone, N-methyl-benzoxazolinone-2-hydrazone and 1,3-dimethylbenzimidazolinone-2-hydrazone.

Included within the purview of this invention are the acid addition salts of the aromatic amines and the hydrazones. Any conventional acid addition salts of the above aromatic amines and hydrazones may be utilized in the process of this invention to quantitatively determine the oxidizing agents. Among the acid addition salts which can be utilized in accordance with this invention are the salts of the aromatic amines and hydrazones with inorganic acids such as hydrochloric acid, hydrobromic acid, sulfuric acid, nitric acid and the like. These acid addition salts can either be used alone or they can be used in conjunction with the corresponding aromatic amine or hydrazone.

In the case of the aromatic amines the hydrochloride addition salts are preferred with m-phenylene diammonium dichloride and N,N-dimethylaniline hydrochloride especially preferred.

In the case of the hdyrazones, acid addition salts of the compounds listed above are preferred with N-methyl-2-benzoythiazolinone-hydrazone hydrochloride especially preferred.

The third component of the composition, the buffer, serves to regulate the final pH of the colored medium. This component consists of citric acid or maleic acid or a combination of both. The ratio of this component to the other ingredients is selected to provide for the colored medium to have a selected predetermined pH range, e.g., a pH range of 3.2 to 4.7 for a uric acid determination and 4.7 to 5.5 for a glucose or cholesterol determination.

The weight ratio of each component in the compositions of this invention can vary over a rather wide range. This variation in weight ratios is determined by the final pH desired and the buffer component used.

Usually, the amine component and the hydrazone component are present in equal weight ratios. The buffer component varies in weight ratio in relation to the other components of the composition of this invention depending on the system being tested and the acid used. Thus, when a pH of from about 3.2 to about 4.7 is required for a uric determination and the buffer used is critic acid, the weight ratios of buffer component to amine component to hydrazone component are 120/0.5–2./0.5–2. The preferred weight ratio for the uric acid determination is 120/1/1. When a pH of from about 4.7 to about 5.5 is required for a glucose or cholesterol determination and the buffer used is citric acid, the weight ratios of buffer component to amine component to hydrazone component are 50/0.5–2/0-.5–2. The preferred weight ratio for the glucose and cholesterol determinations is 50/1/1. When a pH of from about 3.2 to about 4.7 is required for a uric acid determination and the buffer used is maleic acid, the weight ratios of buffer component to amine component to hydrazone component are 60/0.5–6/0.5–6 The preferred weight ratio for the uric acid determination is 60/1/1. When a pH of from about 4.7 to about 5.5 is required for a glucose or cholesterol determination and the buffer used is maleic acid, the weight ratios of buffer component to amine component to hydrazone component are 25/0,5–2/0,5–2 The preferred weight ratio for the glucose or cholesterol determination is 25/1/1.

In cases where the buffer component comprises mixtures of citric and maleic acids, the corresponding weight ratios, in the same order as heretofore are depending of the mixing ratio for a uric acid determination and depending of the mixing ratio for a glucose or cholesterol determination. The preferred ratios are 120–50/1/1 (uric acid) and 60–25/1/1 (glucose or cholesterol).

The compositions encompassed by this invention can be used in the form of a liquid, e.g., an aqueous solution, or as a solid, e.g., as a powder, granulate, tablet or lyophilizate. The compositions are suitable also when applied by impregnation from a solution to an absorbent carrier such as paper, cardboard, textile fabric, wood and the like. The powder form of the composition is the preferred form.

The compositions can also contain other additives which do not interfere with the diagnostic tests being performed, as, for example, bactericidal agents, e.g., sodium azide and sodium ethylmercurithiosalicylate (Thimerosal).

In accordance with the present invention, the quantity of a specific constituent of a biological fluid can be determined from the amount of oxidizing agent produced. The method involves first treating the biological fluid with an appropriate enzyme to thereby produce an oxidizing agent, e.g., hydrogen peroxide, then adding a composition of this invention as the chromogen and finally adding an aqueous buffer solution containing an enzyme (e.g. peroxidase for hydrogen peroxide) which causes, in the present of an oxidizing agent, the oxidative coupling of the amine component and the hydrazone component of the composition of this invention. Upon mixing, the oxidizing agent reacts with the chromogenic composition under the catalytic influence of the added enzyme to form a colored solution. Using a colorimetric procedure, a quantitative measurement of the oxidizing agent content is made and, from this, the content of the specific constituent in the biological fluid is determined.

Any conventional colorimeter or spectrophotometer can be used for the colorimetric measurements. Acceptable colorimeters include Coleman Model 44 and Perkin-Elmer Model 124.

Examples of biological fluids wherein the determination of specific constituents can be carried out using the diagnostic compositions and methods of this invention include blood serum, blood plasma, urine and spinal fluid.

The compositions of this invention can be supplied in a diagnostic kit composed of reagent containers each having one of the following: the composition of this invention and an appropriate enzyme in a buffered mixture. The kit could also have reagent containers with a buffer-peroxidase mixture required for the determination of hydrogen peroxide. Examples of reagents in a kit would be the uricase-buffer system required for an enzymatic uric acid determination, the glucoseoxidase-buffer for an enzymatic glucose determiantion and the cholesterolesterase-cholesteroloxidase-buffer for an enzymatic cholesterol determination. These reagents can be in one kit for multideterminations or separate kits. Each kit has, therefore, the compositions of the invention, a buffer-peroxidase mixture and a buffered enzyme for the specific test.

The following Examples illustrate the invention.

EXAMPLE 1

The following powder compositions were prepared by admixing the components in the proportions listed below.

Composition A 3-methyl-2-benzothiazolinone-hydrazone hydrochloride—30 mg.
m-phenylenediammonium dichloride—30 mg.
citric acid (powder)—3.6g.

Composition B 3-methyl-2-benzothiazolinone-hydrazone hydrochloride—30 mg.
m-phenylenediammonium dichloride—30 mg.
maleic acid (powder)—1.55 g.

Composition C 3-methyl-2-benzothiazolinone-hydrazone hydrochloride—30 mg.
N,N-dimethylaniline hydrochloride—30 mg.
citric acid (powder)—3.6 g.

EXAMPLE 2

Composition A described in Example 1 was used for the analysis of a biological fluid containing uric acid using a continuous flow automated testing system (Technicon Auto-Analyzer). Therein, specimen samples to be tested were drawn up in sequence from separate sample containers in a sample table which rotated at a constant speed to provide 60 samples per hour with a 5:1 wash ratio. A sample so drawn was mixed in flow with 1.3% saline solution and passed through a glass mixing coil of conventional design. After the mixture passed through the mixing coil, it was pumped through a dialyzer module provided with a cellophane or similar membrane through which the uric acid passed in aqueous solution by dialysis. The residual, non-dialyzed portion was discarded. As the uric acid solution passed through the dialyzer module membrance, it was admixed with a uricase solution buffered to a pH of 9.5 with 5 mmol./l. of a borate buffer, which was metered into the system at a flow rate of 1.50 cc/min. Upon leaving the dialyzer, the uric acid-uricase mixture was incubated for 4 minutes in a heating bath at a temperature of 37°C. During the incubation the uric acid was reacted quantitatively to allantoin and hydrogen peroxide. The heated mixture was then mixed with 250 m/. of an aqueous solution of Composition A from Example 1 above, added at flow rate of 0.25cc/min. This mixture was passed through another mixing coil and, after this passage, an aqueous peroxide solution buffered to pH 7.5 with 10 mmol/l of a citrate buffer was added at a flow rate of 0.25 cc/min. The resulting mixture, which had a pH of about 4.0, was then passed through another mixing coil where the hydrogen peroxide reacted with the components of Composition A under the catalytic influence of peroxidase to form a red colored solution. Photometric measurements were then made with a recording photometer at 520 nm using a 15 mm flow cuvette. The uric acid content was obtained from the hydrogen peroxide determination using a calibration curve.

Sixty samples/hour are removed with a continuous flow by this system. The materials which enter into the system are moved by means of suitable pumping to maintain the desired flow velocity. To avoid contamination, the dilution solution and the buffer uricase solution are separated by air-bubbles (flow 0.23 cc/minutes). A detergent, heptadecenylbenzimidazole-sulphonic acid, sodium salt (Ultravon) is added to the dilution, uricase and peroxidase solutions to produce uniform air segmentation of the sample. The amount of detergent added to the dilution solution (aqueous sodium chloride) is 0.15% by volume. The amount of detergent added to the uricase is 1 % by volume and the amount added to the peroxidase is 1 % by volume.

In like manner, compositions B and C from Example 1 are used for the determination of uric acid. The colored solution formed by Composition C is blue and, thus, the photometric measurement are carried out at 590–600 nm.

EXAMPLE 3

Aqueous uric acid standards were prepared containing 5 mg/100 ml., 10 mg/100 mg., 20 mg/100 ml., 30 mg/100 ml. and 40 mg/100 ml. These standards were used in analyses for uric acid using the automated instrument of Example 2 and Compositions A and B to determine reproducibility of results. Results tabulated below show the linear relationship between the concentration of uric acid and the photometer reading obtained using the compositions of this invention to provide chromogenic response.

| Composition A Uric acid concentration mg/100 ml. | Photometer Reading, scale divisions |
|---|---|
| 5 | 112 |
| 10 | 224 |
| 20 | 441 |
| 30 | 668 |
| 40 | 894 |

| Composition B Uric acid concentration mg/100 ml. | Photometer Reading, scale divisions |
|---|---|
| 5 | 106 |
| 10 | 213 |
| 20 | 432 |
| 30 | 660 |
| 40 | 890 |

EXAMPLE 4

The following solutions were prepared:

| | Uric Acid Content |
|---|---|
| Serum 1 | 5.32 mg/100 ml. |

-continued

| Serum 2 | Uric Acid Content 9.44 mg/100 ml. |

To determine the effects of the presence of reducing components in biological fluids on the compositions and methods of this invention, the following quantities of reducing agents were added to separate aliquots of each serum.
  Glutathione — 5 mg/100 ml.
  Acetylsalicyclic acid — 5 mg/100 ml.
  Ascorbic acid — 5 mg/100 ml.
Using Composition A and the procedure described in Example 2, uric acid contents of the sera were made.
Results are tabulated below.

| Test Sample | | Uric Acid found mg/100 ml. | Derivation from theoretical value, % |
| --- | --- | --- | --- |
| Serum 1 + | 5 mg/100 ml. of glutathione | 5.28 | −0.7 |
| Serum 1 + | 5 mg/100 ml. of acetylsalicylic acid | 5.34 | +0.4 |
| Serum 1 + | 5 mg/100 ml. of ascorbic acid | 5.25 | −1.3 |
| Serum 2 + | 5 mg/100 ml. of glutathione | 9.34 | −1.1 |
| Serum 2 + | 5 mg/100 ml. of acetylsalicyclic acid | 9.34 | −1.1 |
| Serum 2 + | 5 mg/100 ml. of ascorbic acid | 9.27 | −1.8 |

Thus, the presence of reducing components in biological fluids has only a minimal effect on the compositions and methods of this invention.

EXAMPLE 5

This example demonstrates both the efficacy of Compositions A, B and C in uric acid determinations and the stability of these compositions even when stored at room temperature as aqueous solutions.

Aqueous solutions of Compositions A, B and C, stored for 2 weeks prior to this test, were used as the chromogens in uric acid determination using the procedure described in Example 2.

The results are tabulated below.

| Sample No. | Composition | Uric acid, theoretical | Uric acid, found |
| --- | --- | --- | --- |
| 1 | A | 4.4 | 4.6 |
| 2 | A | 8.7 | 8.8 |
| 3 | A | 4.8 | 4.4 |
| 4 | A | 10.4 | 10.3 |
| 5 | A | 5.1 | 5.3 |
| 1 | C | 4.4 | 4.4 |
| 2 | C | 8.7 | 8.7 |
| 3 | C | 4.8 | 4.3 |
| 4 | C | 10.4 | 10.3 |
| 5 | B | 5.1 | 5.3 |

EXAMPLE 6

A composition of the invention containing 30 mg. of 3-methyl-2-benzothiazolinone-hydrazone hydrochloride, 30 mg. of m-phenylenediammonium chloride and 1.44 g. of citric acid (powder) was used for the analysis of a biological fluid containing glucose using a continuous flow automated testing system (Technicon AutoAnalyzer). Specimen samples to be tested were drawn up in sequence from separate sample containers on a sample table. The table rotated at a constant speed to provide 60 samples per hour with a 5:1 wash ratio. A sample so drawn was mixed in flow with 1.3% saline solution and passed through a glass mixing coil of conventional design. After the mixture passed through the mixing coil, it was pumped through a dialyzer module provided with a cellophane or similar membrane through which the glucose passed in aqueous solution by dialysis. The residual, non-dialyzed portion was discarded. As the glucose solution passed through the dialyzer membrance, it was admixed with a glucoseoxidase solution buffered to a pH of 7.5 with 1.7g/l. of a citrate buffer which was metered into the system at a flow rate of 1.60cc/min. Upon leaving the dialyzer, the glucose-glucoseoxidase mixture was incubated for at least 2 minutes at room temperature. During the incubation, the glucose was reacted quantitatively to gluconic acid and hydrogen peroxide. The heated mixture was then mixed with an aqueous solution of the amine-hydrazone-citric acid composition described above, added at a flow rate of 0.16cc/min. This mixture was passed through another mixing coil and, after this passage, an aqueous peroxidase solution buffered to a pH of 7.5 with 10 g/l. of a citrate buffer was added at a flow rate of 0.23cc/min. The resulting mixture, which had a pH of about 5.1, was then passed through another mixing coil where the hydrogen peroxide reacted with the components of the composition under the catalytic influence of peroxidase to form a red colored solution. Photometric measurements were then made with a recording photometer at 520 mm using a 15 mm flow cuvette. The glucose content was obtained from the hydrogen peroxide determination using a calibration curve.

Sixty samples/hour are removed with a continuous flow by this system. The materials which enter into the system are moved by means of suitable pumping to maintain the desired flow velocity. To avoid contamination, the dilution solution and the buffered glucoseoxidase solution are separated by air-bubbles (flow 0.230cc/min.). A detergent, polyoxyethylenesorbitan monolaurate (Tween 20) is added to the dilution, glucoseoxidase and peroxidase solutions to produce uniform air segmentation of the sample. The amount of detergent added to the dilution solution is 0.10% by volume and to the enzyme solutions is 1.5% by volume.

EXAMPLE 7

A 20 µl sample containing cholesterol ester and an aqueous suspension of cholesterolesterase containing 0.2 units/ml. buffered to a pH of 7.1 with 10 mmol/l of a phosphate buffer are mixed and incubated at 37°C. This suspension serves as the control. 2.5 ml. of this control are removed, mixed with 20 μl of an aqueous suspension of cholesteroloxidase containing 3 units/ml. buffered to a pH of 7.1 with 10 mmol/l. of a phosphate buffer and incubated at 37°C. This is the test sample.

After incubation for 15 minutes, the test sample and the control are treated with 100 μl of a composition consisting of an aqueous solution containing 30 μg of 3-methyl-2-benzothiazolinone-hydrazone hydrochloride, 30 μg of m-phenylenediammonium chloride and 1.44 mg. of citric acid followed by 500 μl of an aqueous peroxidase solution buffered to a pH of 7.1 using 60 mmol/l. of a phosphate buffer. After 10 minutes, the extinction of the test sample is measured against the control at 500–550 nm using a photometer. The cholesterol content is determined from a standard curve.

I claim:

1. A composition for the colorimetric determination of oxidizing agents comprising:
   a. as the first component, an amine selected from the group consisting of an aromatic amine and an acid addition salt thereof with the proviso that substituents on the aromatic amine are not simultaneously in the ortho and para positions;
   b. as the second component, a compound, capable of oxidatively coupling with the amine of the first component to form a colored entity, selected from the group consisting of a hydrazone and an acid addition salt thereof; and
   c. as the third component, a buffer selected from the group consisting of citric acid, maleic acid and mixtures of citric and maleic acid wherein the amount of the buffer component in the composition is such as to provide for a pre-selected pH range of from about 3.2 to about 5.5 in a resulting colored medium.

2. A composition as in claim 1 wherein the buffer component is citric acid and the weight ratio range of buffer component to amine component to hydrazone component is 25–240/0.5–2/0.5–2.

3. A composition as in claim 1 wherein the buffer component is maleic acid and the weight ratio range of buffer component to amine component to hydrazone is 20–240/0.5–6/0.5–6.

4. A composition as in claim 1 wherein the aromatic amine component is N,N-dimethylaniline and the hydrazone component is N-methyl-2-benzothiazolinone-hydrazone hydrochloride.

5. A composition as in claim 4 wherein the buffer component is citric acid.

6. A composition as in claim 4 wherein the buffer component is maleic acid.

7. A composition as in claim 1 wherein the aromatic amine component is m-phenylenediamine and the hydrazone component is N-methyl-2-benzothiazolinone-hydrazone hydrochloride.

8. A composition as in claim 7 wherein the buffer component is citric acid.

9. A composition as in claim 7 wherein the buffer component is maleic acid.

10. The composition as in claim 1 wherein the aromatic amine component is 30 mg. of m-phenylenediammonium dichloride, the hydrazone component is 30 mg. of 3-methyl-2-benzothiazolinone-hydrazone hydrochloride and the buffer component is 3.6 g. of citric acid powder.

11. The composition as in claim 1 wherein the aromatic amine component is 30 mg. of m-phenylenediammonium dichloride, the hydrazone component is 30 mg. of 3-methyl-2-benzothiazonehydrazone hydrochloride and the buffer component is 1.55 g. of maleic acid powder.

12. The composition as in claim 1 wherein the aromatic amine component is 30 mg. of N,N-dimethylaniline hydrochloride, the hydrazone component is 30 mg. of 3-methyl-2-benzothiazolinone-hydrazone hydrochloride and the buffer component is 3.6 g. of citric acid powder.

13. A method for quantitatively determining the glucose content of a biological fluid which comprises:
   a. mixing the biological fluid with a glucoseoxidase solution having a pH of from about 7 to about 8;
   b. incubating the mixture from step (a) at room temperature;
   c. adding to the product from step (b) a composition comprising as the first component, an amine selected from the group consisting of an aromatic amine and acid addition salt thereof with the proviso that substituents on the aromatic amine are not simultaneously in the ortho and para positions, as the second component, a hydrazone and as the third component, a citric acid buffer;
   d. adding to the mixture from step (c) a buffered peroxidase solution having a pH of from about 7 to about 8 so that the pH of the final mixture ranges from 4.7 to 5.5; and
   e. measuring the glucose content of the fluid by colorimetrically determining the quantity of hydrogen peroxide.

14. The method in accordance with claim 13 wherein the composition comprises 30 mg. of m-phenylenediammonium dichloride, 30 mg. of 3-methyl-2-benzothiazolinonehydrazone hydrochloride and 1.44 g. of citric acid powder.

15. A method for quantitatively determining the uric acid content of a biological fluid which comprises:
   a. mixing the biological fluid with a uricase solution having a pH of from about 9 to about 10;
   b. incubating the mixture from step (a) at a temperature of from about 35°C. to about 40°C.
   c. adding to the product from step (b), a composition comprising as the first component, an amine selected from the group consisting of an aromatic amine and acid addition salt thereof with the proviso that substituents on the aromatic amine are not simultaneously in the ortho and para positions, as the second component, a hydrazone and as the third component, a citric acid buffer;
   d. adding to the mixture from step (c) a buffered peroxidase solution having a pH of from about 7 to about 8 so that the pH of the final mixture ranges from 3.2 to 4.7; and
   e. measuring the uric acid content of the fluid by colorimetrically determining the quantity of hydrogen peroxide present.

16. The method in accordance with claim 15, wherein the composition comprises 30 mg. of m-phenylenediammonium dichloride, 30 mg. of 3-methyl-2-benzothiazolinonehydrazone hydrochloride and 3.6 grams of citric acid powder.

17. A method for quantitatively determining the cholesterol content of a biological fluid which comprises a. mixing the biological fluid with an aqueous suspension of cholesterolesterase at a pH of from about 7 to about 7.5, to form a control mixture.
b. incubating the control mixture from step (a) at a temperature of from about 35°C. to about 40°C;
c. treating an aliquot of the control mixture from step (b) with an aqueous suspension of cholesteroloxidase at a pH of from about 7 to about 7.5, to form a test mixture.
d. incubating the test mixture of step (c) at a temperature of from about 35°C. to about 40°C.;
e. adding to the test mixture of step (d) and the control mixture of step (b) a composition comprising as the first component, an amine selected from the group consisting of an aromatic amine and acid addition salt thereof with the proviso that substituents on the aromatic amine are not simultaneously in the ortho and para positions, as the second component, a hydrazone and as the third component, a citric acid buffer;
f. adding to each of the mixtures from step (e) a peroxidase solution having a pH of from about 7 to about 7.5;
g. maintaining the reaction for 10 minutes to allow the color to develop; and
h. measuring the cholesterol content of the fluid by colorimetrically comparing the test mixture with the control mixture.

18. The method in accordance with claim 15 wherein the composition comprises 30 mg. of m-phenylenediammonium dichloride, 30 mg. of 3-methyl-2-benzothiazolinonehydrazone hydrochloride and 1.44 mg. of citric acid powder.

19. A diagnostic test kit for the determination of hydrogen peroxide which comprises:
a. a container having a composition comprising:
   i. as the first component, an amine selected from the group consisting of an aromatic amine and an acid addition salt thereof with the proviso that substituents in the aromatic amine are not simultaneously in the ortho and para positions;
   ii. as the second component, a compound, capable of oxidatively coupling with the amine of the first component to form a colored entity, selected from the group consisting of a hydrazone and an acid addition salt thereof; and
   iii. as the third component, a buffer selected from the group consisting of citric acid, maleic acid and mixtures of citric and maleic acid; and
b. A container having buffer-peroxidase mixture.

20. A diagnostic test kit for the determination of uric acid in biological fluids which comprises, in addition to the containers of claim 19, a container having a buffer-uricase mixture.

21. A diagnostic test kit for the determination of glucose in biological fluids, which comprises in addition to the containers of claim 19, a container having buffer-glucoseoxidase mixture.

22. A diagnostic test kit for the determination of cholesterol in biological fluids which comprises, in addition to the containers of claim 19
a. a container having a buffer-cholesterolesterase mixture; and
b. a container having a buffer-cholesteroloxidase mixture.

* * * * *